US009192362B2

(12) United States Patent
Paul, Jr. et al.

(10) Patent No.: US 9,192,362 B2
(45) Date of Patent: Nov. 24, 2015

(54) DEVICE AND METHOD FOR CLOSURE OF VESSEL ACCESS SITE

(75) Inventors: Ram H. Paul, Jr., Bloomington, IN (US); Brian L. Bates, Bloomington, IN (US); Bradley L. Trembacki, Dyer, IN (US)

(73) Assignee: COOK MEDICAL TECHNOLOGIES LLC, Bloomington, IN (US)

( * ) Notice: Subject to any disclaimer, the term of this patent is extended or adjusted under 35 U.S.C. 154(b) by 332 days.

(21) Appl. No.: 13/059,157

(22) PCT Filed: Aug. 17, 2009

(86) PCT No.: PCT/US2009/053995
§ 371 (c)(1),
(2), (4) Date: Mar. 28, 2011

(87) PCT Pub. No.: WO2010/021969
PCT Pub. Date: Feb. 25, 2010

(65) Prior Publication Data
US 2011/0178547 A1    Jul. 21, 2011

Related U.S. Application Data

(60) Provisional application No. 61/089,745, filed on Aug. 18, 2008.

(51) Int. Cl.
*A61B 17/00* (2006.01)
*A61B 18/14* (2006.01)
(Continued)

(52) U.S. Cl.
CPC ......... *A61B 17/0057* (2013.01); *A61B 18/1442* (2013.01); *A61B 18/1445* (2013.01); *A61B 18/1447* (2013.01); *A61B 2017/00986* (2013.01);
(Continued)

(58) Field of Classification Search
CPC ............... A61B 17/08; A61B 17/0057; A61B 2017/00575; A61B 2017/00579; A61B 2017/00986; A61B 2017/301; A61B 2017/303; A61B 2017/305; A61B 2017/2926; A61B 2017/2927; A61B 2017/2905; A61B 18/1442; A61B 18/1445; A61B 18/1447
USPC ................ 606/213, 215, 216, 205–208, 127; 81/44, 451–455, 457; 294/86.4
See application file for complete search history.

(56) References Cited

U.S. PATENT DOCUMENTS 3,879,516 A * 4/1975 Wolvek .......................... 264/135
4,222,380 A * 9/1980 Terayama ..................... 604/115
(Continued)

FOREIGN PATENT DOCUMENTS

| EP | 1312314 A1 | 5/2003 | ............ A61B 17/30 |
| WO | WO 2005/013832 A1 | 2/2005 | ............ A61B 17/00 |

*Primary Examiner* — Tuan V Nguyen
*Assistant Examiner* — Lucas Paez
(74) *Attorney, Agent, or Firm* — Brinks Gilson & Lione

(57) ABSTRACT

A device for closure of an opening formed in a body vessel includes a grasping member and a sheath movable thereover. The grasping member comprises a tubular body having a plurality of grasping fingers extending from a distal end of the tubular body. The fingers radially extend from the tubular body at a first angle, and are collapsible therefrom to a second angle. The fingers have a distal tip configured for grasping an outer wall of the body vessel surrounding the vessel opening when the fingers are at the first angle. The sheath is slidable over the tubular body and at least a portion of the grasping fingers for collapsing the fingers from the first angle to the second angle, thereby causing the collapsed fingers to at least substantially close the opening.

25 Claims, 8 Drawing Sheets

(51) Int. Cl.
*A61B 17/30* (2006.01)
*A61B 17/29* (2006.01)

(52) U.S. Cl.
CPC . *A61B 2017/2905* (2013.01); *A61B 2017/2926* (2013.01); *A61B 2017/2927* (2013.01); *A61B 2017/301* (2013.01); *A61B 2017/303* (2013.01); *A61B 2017/305* (2013.01)

(56) References Cited

U.S. PATENT DOCUMENTS

| | | | |
|---|---|---|---|
| 4,444,380 A | | 4/1984 | Chambers et al. |
| 4,467,802 A | * | 8/1984 | Maslanka .................... 606/206 |
| 4,509,517 A | * | 4/1985 | Zibelin ....................... 606/127 |
| 4,608,965 A | | 9/1986 | Anspach, Jr. et al. ............ 128/4 |
| 5,156,609 A | * | 10/1992 | Nakao et al. ................. 606/142 |
| 5,300,086 A | * | 4/1994 | Gory et al. ................... 606/200 |
| 5,667,525 A | | 9/1997 | Ishibashi ..................... 606/206 |
| 5,776,075 A | | 7/1998 | Palmer ........................ 600/564 |
| 5,782,861 A | * | 7/1998 | Cragg et al. .................. 606/216 |
| 5,944,728 A | * | 8/1999 | Bates .......................... 606/127 |
| 5,984,939 A | | 11/1999 | Yoon ........................... 606/170 |
| 5,984,950 A | * | 11/1999 | Cragg et al. .................. 606/216 |
| 6,033,427 A | | 3/2000 | Lee ............................ 606/213 |
| 6,846,321 B2 | * | 1/2005 | Zucker ........................ 606/213 |
| 7,060,084 B1 | | 6/2006 | Loshakove et al. ............ 606/213 |
| 7,396,359 B1 | | 7/2008 | Derowe et al. ................ 606/213 |
| 7,625,392 B2 | * | 12/2009 | Coleman et al. .............. 606/213 |
| 8,192,457 B2 | | 6/2012 | Coleman et al. .............. 606/213 |
| 8,298,244 B2 | * | 10/2012 | Garcia et al. ................. 606/127 |
| 8,366,706 B2 | * | 2/2013 | Buchbinder et al. ............ 606/27 |
| 8,366,742 B2 | * | 2/2013 | Coleman et al. .............. 606/213 |
| 2001/0053923 A1 | * | 12/2001 | Sato et al. .................... 606/215 |
| 2003/0158563 A1 | | 8/2003 | McClellan et al. ............. 606/151 |
| 2005/0049612 A1 | * | 3/2005 | Urbanski et al. .............. 606/127 |
| 2005/0251202 A1 | * | 11/2005 | Ewers et al. .................. 606/213 |
| 2007/0027456 A1 | | 2/2007 | Gartner et al. ................ 606/113 |
| 2007/0106328 A1 | * | 5/2007 | Wardle et al. ................. 606/213 |
| 2009/0018604 A1 | * | 1/2009 | Mitelberg et al. .............. 607/40 |
| 2011/0178547 A1 | * | 7/2011 | Paul et al. .................... 606/213 |
| 2012/0179172 A1 | * | 7/2012 | Paul et al. .................... 606/142 |

* cited by examiner

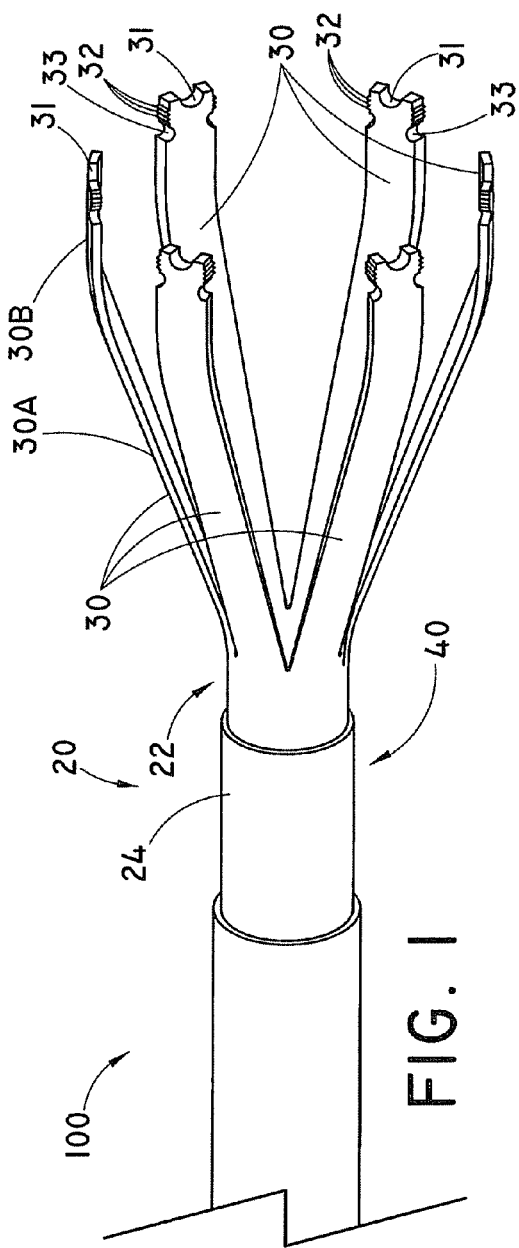
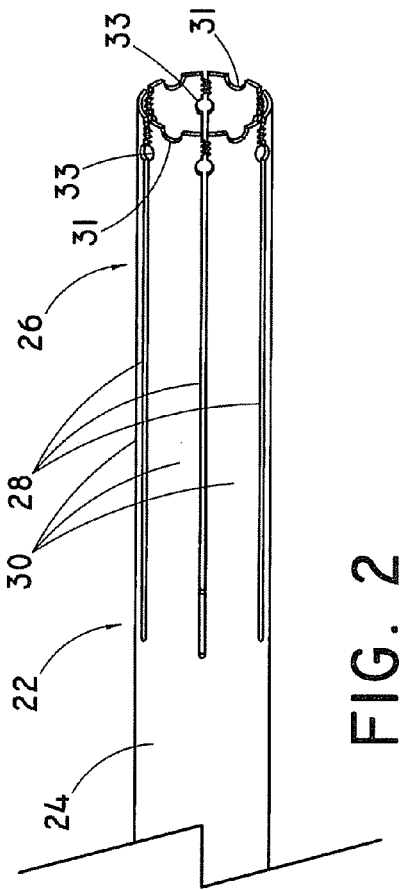
FIG. 1
FIG. 2

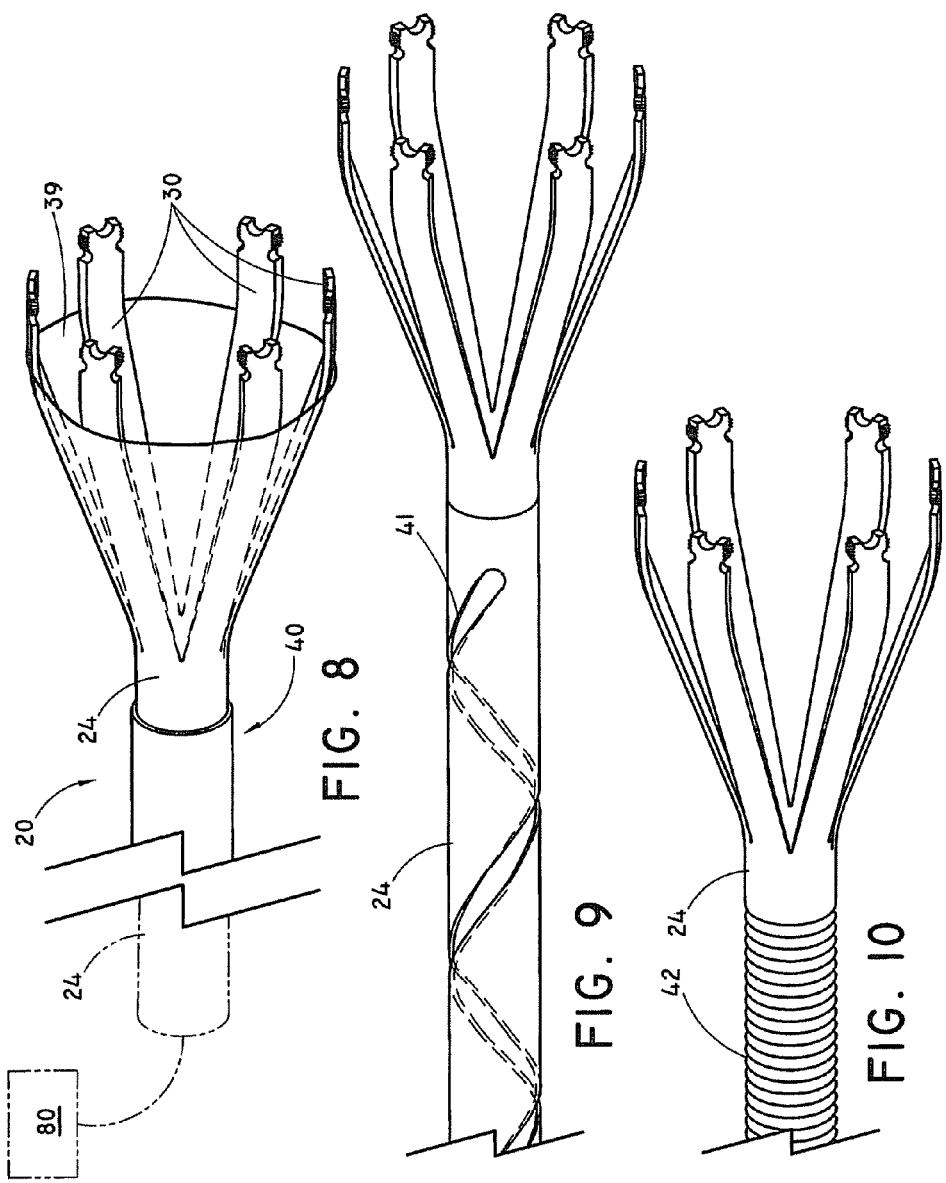

US 9,192,362 B2

DEVICE AND METHOD FOR CLOSURE OF VESSEL ACCESS SITE

BACKGROUND

1. Technical Field

This invention relates to the field of medical apparatuses. More particularly, the invention relates to a device and method for closure of an access site of a body vessel, such as a blood vessel.

2. Background Information

Numerous advances of considerable note have occurred in medical surgical techniques over the last few decades. Among the most significant advances has been the adoption, and now-routine performance, of a variety of minimally invasive procedures. These minimally invasive procedures are distinguishable from conventional open surgical procedures in that access to a body vessel of a patient, such as a blood vessel, is achieved through a relatively small incision through the wall of the vessel. A tubular medical device (or tubular portion of a device) may be inserted or introduced through the incision into the interior space of the vessel for carrying out a medical procedure. The tubular device, or device portion, keeps the incision open while permitting access to the vessel via the interior passageway of the tubular device.

When carrying out such minimally invasive procedures, communication with the lumen of the vessel is typically attained by inserting an access device, such as an introducer sheath, through the opening in the vessel wall. One typical procedure for inserting the introducer sheath is the well-known Seldinger percutaneous entry technique. In the Seldinger technique, a needle is initially inserted into the vessel, and a wire guide is inserted into the vessel through a bore of the needle. The needle is withdrawn, and an introducer assembly is inserted over the wire guide into the vessel opening. Typically, the introducer assembly includes an outer introducer sheath, and an inner dilator having a tapered distal end. The tapered end of the dilator stretches the opening in the vessel in controlled fashion, so that introduction of the larger diameter introducer sheath may then be carried out with a minimum of trauma to the patient.

Following advancement of the introducer sheath into the opening, the dilator is removed, leaving at least the distal portion of the larger diameter introducer sheath in place in the vessel. The introducer sheath is generally provided with a valve at its proximal end for inhibiting leakage of body fluids through the introducer. A catheter may be inserted through the valve and the lumen of the introducer sheath. The catheter is threaded over the wire guide, and the distal end of the catheter is inserted into position in the vessel for carrying out the medical procedure. As a result, the introducer sheath can facilitate insertion of various devices into the vessel while minimizing trauma to the vessel wall and minimizing blood loss during the procedure. Upon completion of the medical procedure, the catheter and introducer sheath are generally removed, leaving a puncture at the vascular access site.

The puncture at the vascular access site is typically closed by suturing, or by manually providing pressure on the site until clotting and/or wound sealing occurs. Suturing is more often utilized for larger punctures, whereas manual pressure is more often utilized in connection with smaller punctures. The manual method, however, can take half an hour or more, and requires the patient to remain substantially immobilized for at least that period of time while pressure is applied by medical personnel to the access site. In addition, it may be necessary for the patient to remain in the hospital for a period of time thereafter for observation. Furthermore, there may be a possibility of clot formation at the puncture site.

Utilizing sutures and/or collagen plugs to close the opening may have procedure variability, which may require additional time to close the vessel. When sutures are utilized to close a larger vascular access site, they typically are of the "purse-string" type. In this type of suture, a single thread is stitched to surround the access site, and then pulled tight (like a purse-string) to close the access site. Performing this suture typically requires a good deal of skill and practice on the part of the physician. It also may be difficult to perform this type of suturing in a key-hole type procedure, or in other types of surgery where there is limited access to the wound site.

It is desired to provide a device and method for closure of a vessel access site that overcomes the problems of the prior art.

BRIEF DESCRIPTION OF THE DRAWINGS

FIG. 1 is a side view of one embodiment of a device for closure of a vessel access site according to the present invention;

FIG. 2 is a side view of the distal end of the tubular body portion of the device of FIG. 1 prior to shaping the tubular body portion for use in the inventive device;

FIG. 8 illustrates an alternative embodiment of the closure device of FIG. 1, including an expandable member extending around the fingers of the device;

FIG. 9 illustrates an alternative embodiment of the closure device of FIG. 1, including a spiral slot formed along the tubular body of the grasping member;

FIG. 10 illustrates an alternative embodiment of the closure device of FIG. 1, including a helical member disposed along a length of the tubular body of the grasping member;

DETAILED DESCRIPTION OF THE DRAWINGS AND THE PRESENTLY PREFERRED EMBODIMENTS

Figure 3:
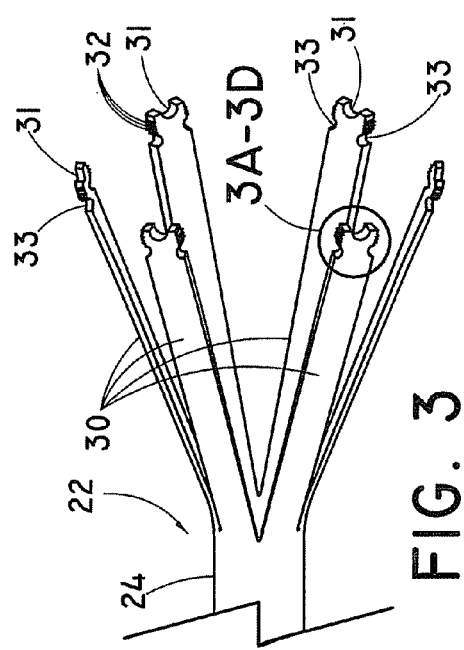
FIG. 3 illustrates partial shaping of the tubular body portion illustrated in FIG. 2.

For the purposes of promoting an understanding of the principles of the invention, reference will now be made to the embodiments illustrated in the drawings, and specific language will be used to describe the same. It should nevertheless be understood that no limitation of the scope of the invention is thereby intended, such alterations and further modifications in the illustrated device, and such further applications of the principles of the invention as illustrated therein being contemplated as would normally occur to one skilled in the art to which the invention relates.

In the following discussion, the terms "proximal" and "distal" will be used to describe the opposing axial ends of the inventive vessel closure device, as well as the axial ends of various component features. The term "proximal" is used in its conventional sense to refer to the end of the device (or component thereof) that is closest to the operator during use of the sheath. The term "distal" is used in its conventional sense to refer to the end of the device (or component thereof) that is initially inserted into the patient, or that is closest to the patient during use.

FIG. 1 illustrates a side view of one embodiment of a device 20 for closure of a vessel access site according to the present invention. As described herein, use of device 20 allows for rapid and minimally invasive closure of an opening formed through a wall of a body vessel, such as a blood vessel, during a medical procedure that has previously been carried out at the site.

As illustrated in FIG. 1, device 20 includes two main components, namely, a grasping member 22 and a sheath 40 overlying a proximal portion of the grasping member. Also illustrated in FIG. 1 is the distal end of a conventional introducer sheath 100 through which closure device 20 may be introduced into a body passageway for passage to the affected vessel site in conventional fashion.

To provide a better understanding of structure of the grasping member 22, FIGS. 2 and 3 illustrate two stages that may be carried out for forming the grasping member. Preferably, grasping member 22 is formed from a relatively rigid biocompatible tubular structure, such as a metal, metal alloy, or relatively rigid polymeric tube. Non-limiting examples of particularly suitable materials for forming grasping member 22 include a spring metal, such as stainless steels (e.g., 316, 316L or 304); nickel-titanium alloys including shape memory or superelastic types (e.g., nitinol or elastinite); inconel; noble metals including copper, silver, gold, platinum, palladium and iridium; refractory metals including molybdenum, tungsten, tantalum, titanium, rhenium, or niobium; stainless steels alloyed with noble and/or refractory metals; magnesium; amorphous metals; plastically deformable metals (e.g., tantalum); nickel-based alloys (e.g., including platinum, gold and/or tantalum alloys); iron-based alloys (e.g., including platinum, gold and/or tantalum alloys); cobalt-based alloys (e.g., including platinum, gold and/or tantalum alloys); cobalt-chrome alloys (e.g., elgiloy); cobalt-chromium-nickel alloys (e.g., phynox); alloys of cobalt, nickel, chromium and molybdenum (e.g., MP35N or MP20N); cobalt-chromium-vanadium alloys; cobalt-chromium-tungsten alloys; platinum-iridium alloys; platinum-tungsten alloys; magnesium alloys; titanium alloys (e.g., TIC, TIN); tantalum alloys (e.g., TaC, TaN); L605; magnetic ferrite; bioabsorbable materials, including magnesium; or other biocompatible metals and/or alloys thereof.

As shown in FIGS. 2 and 3, grasping member 22 comprises an integral member including a tubular main body portion 24, and a distal portion 26 extending therefrom. Typically, tubular main body portion 24 will have a generally circular cross section, although tubular body members having other geometrical cross sections, such as an elliptical, square, etc., may alternatively be utilized. A series of slits 28 are cut, e.g., by laser cutting, along the length of distal portion 26. Preferably, six slits 28 are cut along the circumference of distal portion 26 as shown. Ultimately, following final shaping of the grasping member as further described herein, slits 28 define six grasping fingers 30. Slits 28 may be formed to have any desired length to enable closure device 20 to perform the functions described herein. Preferably, slits (and therefore fingers 30) will have a length of about 3-15 mm, and more preferably, about 6 mm. Those skilled in the art will appreciate that other numbers and dimensions of slits may be formed, resulting in the formation of other numbers and/or sizes of grasping fingers.

Grasping member 22 will typically have a length such that the proximal end of the grasping member extends in the proximal direction beyond the proximal end of the introducer sheath 100. This arrangement permits easy access to the proximal end of grasping member by the user. Thus, for example, grasping member 22 will typically have a length between about 15 and 120 cm. The exact length of the grasping member is generally not critical, but as stated, such length will typically slightly exceed the length of the introducer sheath in order to provide access at the proximal end as described.

The precise outer diameter of the grasping member is also typically not critical. Preferably, however, such outer diameter will generally be within a range of about 0.75 and 2 mm, such as about 1.2 mm.

Along with the series of slits 28, additional features may also be cut along the length of distal portion 26. When present, these optional features assist in grasping and securing tissue surrounding the vessel access site, without piercing the vessel wall. Thus, for example, as shown in the embodiments depicted in FIGS. 3, 3A, and 6, a cut-out portion, such as the generally semicircular groove 31 shown in the figures, may be cut into a generally flat distal tip 34 of each finger. When present, the grooves 31, or similar structure, function in the nature of a "stop" along the generally flat distal tip to limit penetration of the finger 30 into the tissue of the vessel wall during use, by allowing the tissue to fold into the grasping finger without piercing the tissue.

One or more teeth 32 (three are shown in the figures), or similar structure (e.g., teeth in the nature of barbs) may be cut or otherwise formed into the sides of the fingers. When present, teeth 32 assist in grasping the tissue, and preventing the tissue from slipping out when it is caught between the fingers. Any number and shape of teeth or other structure may be provided, so long as the structure is capable of grasping the tissue as described.

Figure 11:
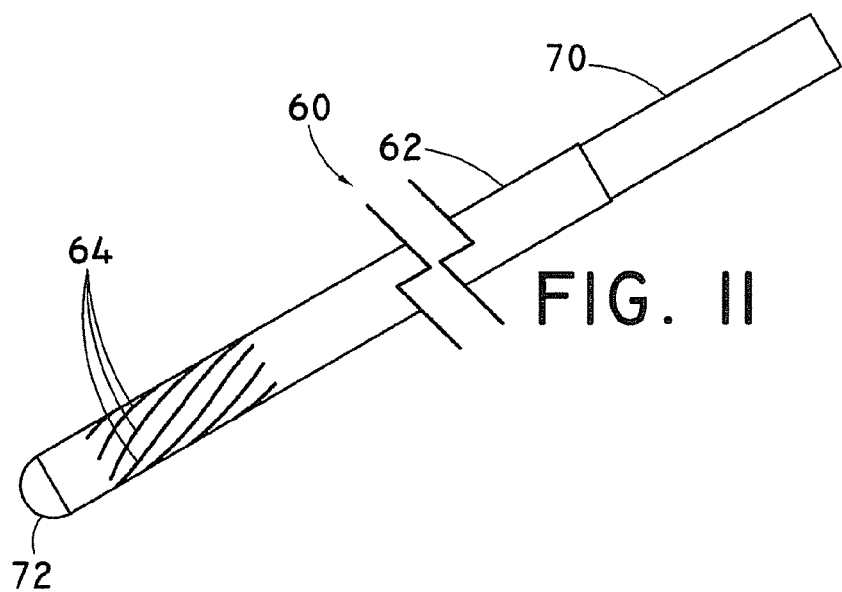
FIG. 11 illustrates an anchor member that may be incorporated into the closure device, shown in a non-expanded condition.
Figure 12:
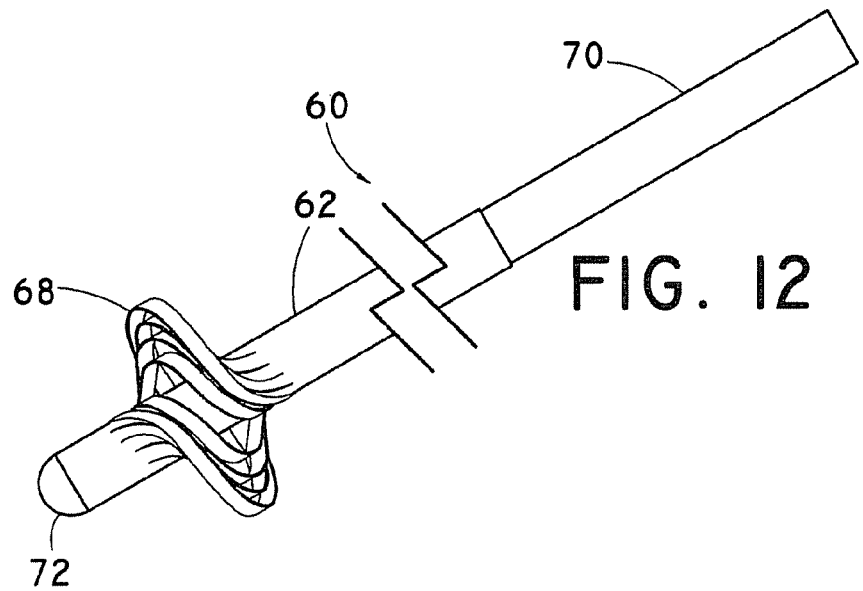
FIG. 12 illustrates the anchor member of FIG. 11, in an expanded condition.

A cut-out portion, such as arc 33, may be cut on each lateral side of a finger. When present, arc 33 provides a space, or reservoir, into which the tissue may fold. In addition, this structure allows more room for an anchor assembly to slide through the fingers when they are in a collapsed condition. The optional anchor assembly is further illustrated, e.g., in FIGS. 11 and 12, and is further described herein.

Figure 3A:
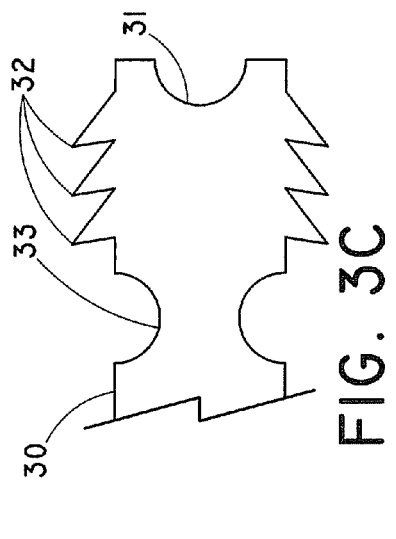
FIGS. 3A-3D are enlarged side views of alternative configurations of the distal portions of the fingers of the grasping member.
Figure 3B:
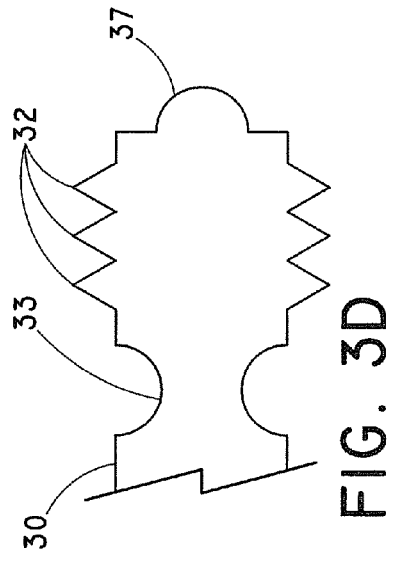
Figure 3C:
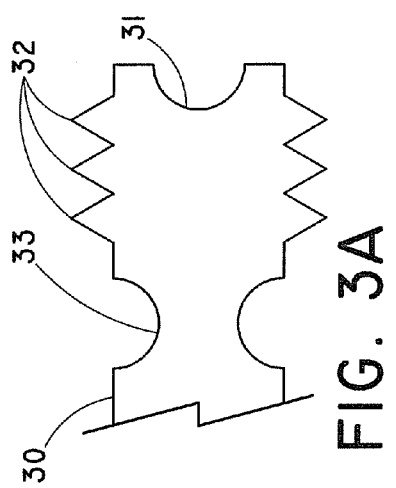
Figure 3D:
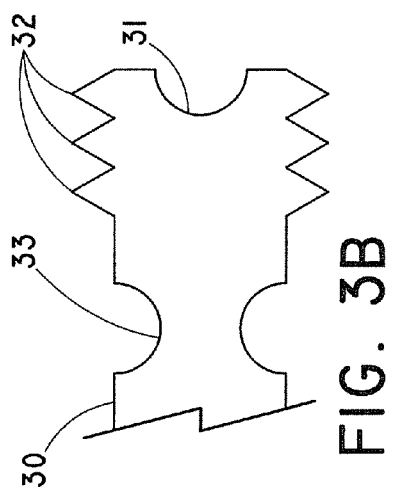

FIGS. 3A-3D illustrate non-limiting examples of various alternative configurations of the distal portions of the grasping member fingers. Each of these figures includes examples of such features. The variations provided in FIGS. 3A-3D are not intended to be exclusive, but rather, to illustrate four possible distal end configurations. Each of these configurations may be preferred for closure of a particular vessel opening. FIG. 3A is an enlarged view of the distal portion of fingers 30 illustrated in FIGS. 3-10. FIG. 3B is similar to FIG. 3A, except that the teeth 32 are moved closer to the distal end of the finger 30. In FIG. 3C, the teeth 32 are tilted in the proximal direction, to function in the manner of barbs. In FIG. 3D, end groove 31 has been replaced with projection 37.

In one preferred embodiment, cut-out portion 31 may have a width of about 0.010 inch (0.25 mm), and a depth of about 0.005 inch (0.13 mm). Teeth 32 may have height of about 0.005 inch (0.13 mm). Arc 33 may have a width of about 0.10 inch (0.25 mm) and a depth of about 0.0035 inch (0.09 mm) length. Projection 37 may have a length (in the distal direction) of about 0.005 inch (0.13 mm).

Some fingers can be provided with one feature, or set of features, whereas other fingers may have other features, or no features. In addition, all fingers 30 need not necessarily have the same length, width, shape, or other dimensions. Preferably, when fingers 30 are of different lengths, teeth 32 will be positioned and aligned along each finger such that the teeth of each finger will correspond in the longitudinal direction with the teeth on an adjacent finger in the manner shown in the figures. However, other arrangements are also possible when the teeth are not so aligned.

Those skilled in the art will appreciate that the number, arrangement, shape, and dimensions, of the fingers, as well as the additional features provided on the fingers, such as features 31, 32, 33, and 37 described hereinabove, are only intended to represent examples of possible arrangements, and are not to be construed as limiting grasping member 22 to any particular structure. For example, additional features may be added to the grasping member 22 to assist in grasping and/or securing tissue surrounding a vessel opening. Additional, or fewer, features may be provided on fingers 30 in a particular case. In addition, not all fingers need have the same arrangement of features. It is believed that one skilled in the art is readily capable of optimizing an arrangement of features for a particular case without undue experimentation.

Following laser cutting of slits 28 as described, and the cutting of grasping features (e.g., features 31-33 in FIG. 2) into fingers 30, the fingers may then be set into a desired shape. This may be accomplished, e.g., by inserting an appropriately shaped conical form (insert) into the distal portion 26. The assembly comprising the tubular body and conical form is then placed in an oven and heated for an appropriate time, and at an appropriate temperature, to provide the fingers with an internal memory. Thus, when not covered by a sheath, the fingers will have a tendency to expand outwardly from the longitudinal axis of the grasping member, as shown in FIG. 3. The time and temperature required for heating will vary depending on factors such as the composition of tubular body 24, and the dimensions of the fingers. Optimization of these factors is believed to be readily within the expertise of one skilled in the art.

In one preferred embodiment, each finger 30 is shaped such that it includes a segment 30A (FIG. 1) that angles away from the longitudinal axis of tubular main body portion 24. Preferably, segment 30A angles from the longitudinal axis at a predetermined angle, e.g., between about 15 and 60 degrees, and more preferably, about 30 degrees. The particular angle of the fingers of a grasping apparatus from the longitudinal axis will be a function of the shape and dimensions of the particular conical form selected for use, and may be formed based upon an intended use of the closure device. In a preferred embodiment, a more distal segment 30B of the grasping fingers is further angled from the angle described above, as shown in FIG. 4. This enhances the ability of the fingers to grasp the tissue surrounding the vessel opening. When closure device 20 is in use, distal segment 30B may be aligned in one embodiment such that it is substantially perpendicular to the access site. In one preferred embodiment (e.g., FIG. 1), fingers 30 are aligned in a manner such that the respective finger distal tips 34 collectively are arranged in a generally circular manner, wherein the circle has a diameter of, e.g., of about 5 mm.

Although distal portion 26 (and therefore fingers 30) of grasping member 22 may be initially formed from the distal portion of tubular main body portion 24 as shown in FIGS. 2 and 3 and described herein, those skilled in the art will appreciate that this is merely one manner in which the distal portion 26 may be formed, and that other constructions may be utilized. For example, distal portion 26 (and fingers 30) may be separately formed, and thereafter securely engaged with the distal end of tubular body portion 24 by any well-known attachment mechanism, such as an adhesive or via mechanical attachment.

Sheath 40 of closure device 20 is preferably formed of a lubricous, relatively rigid tubular material. Non-limiting examples of suitable materials include polyether ether ketone (PEEK), polyamide (nylon), polyimide, polyethylene terephthalate (PET), polysulfone, tetrafluoroethylene (TFE), and fluorinated ethylene propylene (FEP).

As with the grasping member, the precise outer diameter of the sheath 40 is also typically not critical. Preferably, however, such outer diameter will generally be within a range of about 1.5 and 3 mm, such as about 1.7 mm. Sheath 40 includes an inner lumen dimensioned to receive the main tubular (proximal) portion 24 of grasping member 22. Sheath 40 will also preferably have a length such that the proximal end of the sheath 40 extends in the proximal direction beyond the proximal end of the introducer sheath 100, for permitting easy access to the proximal end of the sheath by the user.

During use of closure device 20, sheath 40 is slidable in a distal direction relative to the grasping member 22. FIG. 1 illustrates sheath 40 extending over a portion of the tubular main body 24 of grasping member 22, but not over grasping fingers 30. As a result, fingers 30 are fully radially extended, due to the internal memory set in the fingers as described above.

Figure 4:
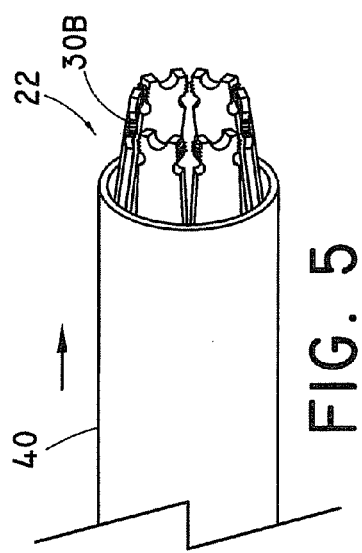
FIGS. 4 and 5 show successive stages of the closure of the device.

In the view depicted in FIG. 4, sheath 40 has been advanced distally relative to grasping member 22, such that a relatively short length (e.g., about 1 mm) of fingers segment 30A is covered by the sheath. This action causes fingers 30 to begin to collapse within the lumen of the sheath 40 from the predetermined angle specified above. In the view depicted in FIG. 5, sheath 40 has been further advanced over fingers 30 such that the sheath encompasses a portion of segment 30B of fingers 30. In this condition, the overlying sheath 40 essentially collapses fingers 30 into a closed position around the vessel opening. In use, the collapsing motion of the grasping fingers pulls, or gathers, the tissue immediately adjacent an opening in a vessel radially inwardly to at least substantially close the access opening, in a manner to be described.

Figure 6:
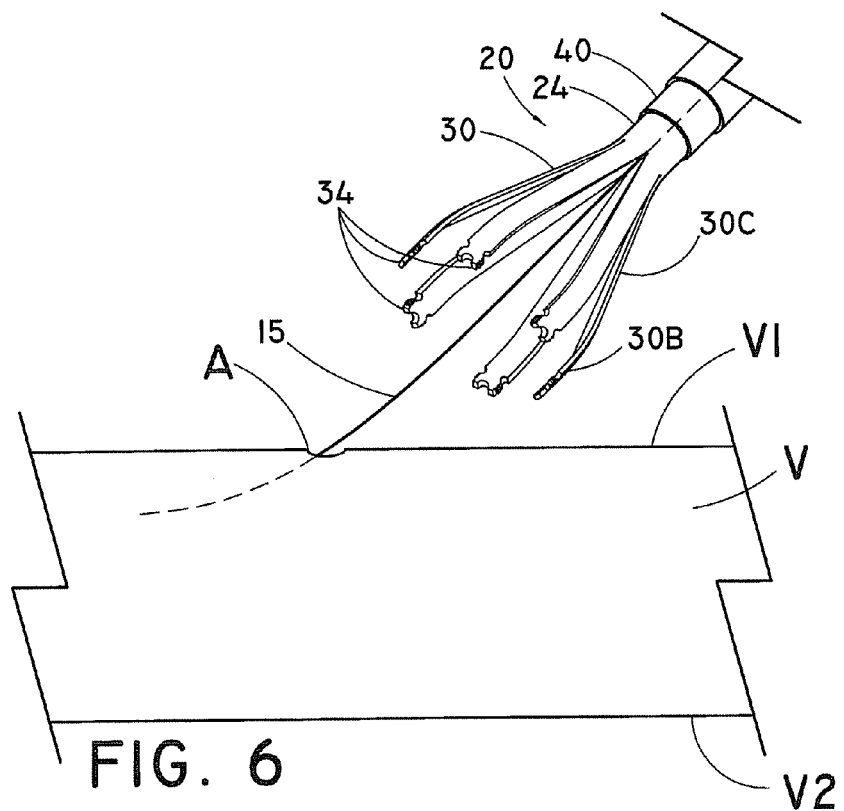
FIGS. 6 and 7 show use of the device to close a vessel opening.
Figure 7:
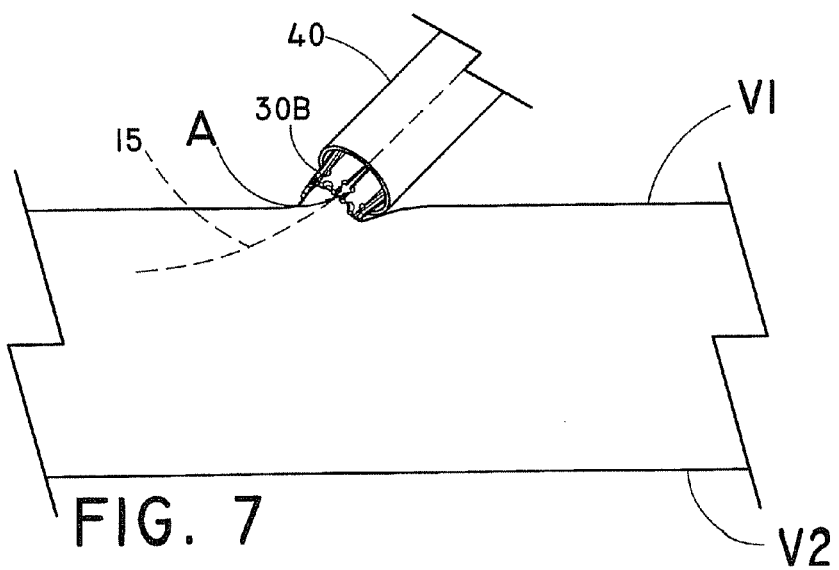

One example of the use of closure device 20 to close an opening A in a vessel V is illustrated in FIGS. 6 and 7. The opening A intended for closure has been made through first vessel wall V1 during the course of a medical procedure that has previously been carried out. The opposite vessel wall is designated in the figures as V2.

As illustrated in FIG. 6, a previously-positioned wire guide 15 has been inserted through opening A into the interior of the vessel by conventional means. Device 20 passes over wire guide 15 such that the respective distal tips 34 of grasping fingers 30 approach the outer wall V1 of vessel V.

As illustrated in FIG. 7, finger distal tips 34 have been further advanced to grasp the outer surface of vessel wall V1, and sheath 40 has been advanced over fingers 30 to collapse the fingers as shown. In this view, fingers 30 collapse in a manner such that finger segments 30B grasp, or gather, the tissue surrounding vessel opening A, without piercing the vessel wall. When features, such as features 31-33 are included on fingers 30, tissue may be gathered between the fingers as described. When the fingers are collapsed as shown, the tissue surrounding the vessel opening is brought together in a manner such that the vessel opening is at least substantially closed. Once the tissue has been gathered as described, the fingers can maintain contact with the site to allow clotting and wound sealing to take place.

Figure 5:
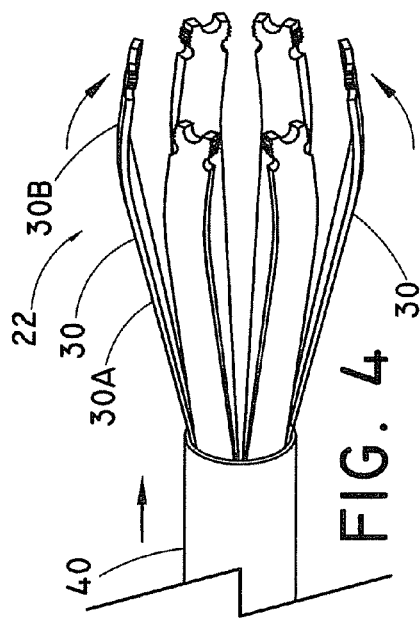

FIG. 8 illustrates a variation of the closure device of FIG. 1. In this variation, a skirt 39 is provided around at least a portion of fingers 30 of closure device 20. Preferably, skirt 39 also extends along a length of tubular main body portion 24. In the version shown in FIG. 8, skirt 39 extends around the outer surface of fingers segment 30A (FIG. 1), and does not extend along segment 30B. Skirt 39 comprises an expandable material, such as ePTFE, a polyether block amide, polyisoprene or silicone, that is capable of expanding as fingers open radially as shown in FIG. 8. Skirt 39 prevents surrounding tissues from getting caught between the upper part (e.g., segment 30A) of fingers 30, and thereby preventing closure of the fingers, as shown in FIGS. 5 and 7.

Although FIG. 8 illustrates the presence of skirt 39 around the outer surface of the fingers, the skirt can alternatively be positioned around the inner surface of the fingers. As still another alternative, a separate skirt can be provided around each of the outside and inside of the fingers. As yet another alternative, the skirt may extend further toward the distal end of the fingers than shown in FIG. 8.

Additional variations that may be made to the grasping member 22 are illustrated in FIGS. 9 and 10. On some occasions it may be desirable to allow the main tubular body portion 24 of the grasping member 22 to bend, or articulate, as the distal end of closure device 20 approaches a vessel opening intended for closure. This bending, or articulating, ability may facilitate the positioning of the closure device relative to the opening, and thereby facilitate grasping of a particular tissue segment surrounding the opening.

FIGS. 9 and 10 illustrate two possible ways in which this bending or articulation may be accomplished. In FIG. 9, a spiral slot 41 is formed along a discrete length of tubular member 24. Spiral slot 41 weakens the length of the tubular member 24 to permit a degree of bending of the tubular member as may be desired. In FIG. 10, a helical coil 42 is formed along a discrete length of tubular member 24. Coil 42 may be formed to have any tension requirements desired for permitting a desired degree of bending of the affected tubular member length 24.

Preferably, the slot 41 or coil 42 will only extend along, or interrupt, the tubular member for a sufficient length, e.g., about 2 mm to 2 cm, to enable bending of a discrete length of the tubular member. Those skilled in the art will appreciate that the spiral slot 41 and coil 42 illustrated herein are only examples of well-known structures that may be utilized for bending a shaft member as described, and that other structures capable of allowing bending or articulation may be substituted for the spiral slot and coil as shown.

Another embodiment of the closure device is illustrated in FIGS. 11-14. In this embodiment, an anchor 60 is provided for facilitating the wound closing. In one form, anchor 60 is formed from a cannula 62 having a series (such as 8) of generally helical or spiral slits 64 laser cut or otherwise formed along the distal end of the cannula. Preferably, cannula 62 is formed from a relatively rigid biocompatible tubular structure, such as a metal, metal alloy, or relatively rigid polymeric tube. Nitinol or other spring type metals are particularly preferred materials for forming cannula 62.

In the embodiment shown, anchor 60 includes a rod 70 or like structure that extends through the lumen of cannula 62. A distal end 72 of rod 70 extends beyond the distal end of cannula 62, and is fixedly attached thereto, e.g., by welding. When the operator advances the cannula in the distal direction relative to the rod (FIG. 12), the spiral slits 64 bow radially outwardly to form a generally large diameter anchored portion 68. Large diameter portion 68 may be maintained as long as cannula 62 is maintained in the distal position relative to rod 70. When cannula 62 is released, or otherwise moved in a proximal direction relative to rod 70, spiral slits 64 substantially re-seat to the position shown in FIG. 11.

Figure 13:
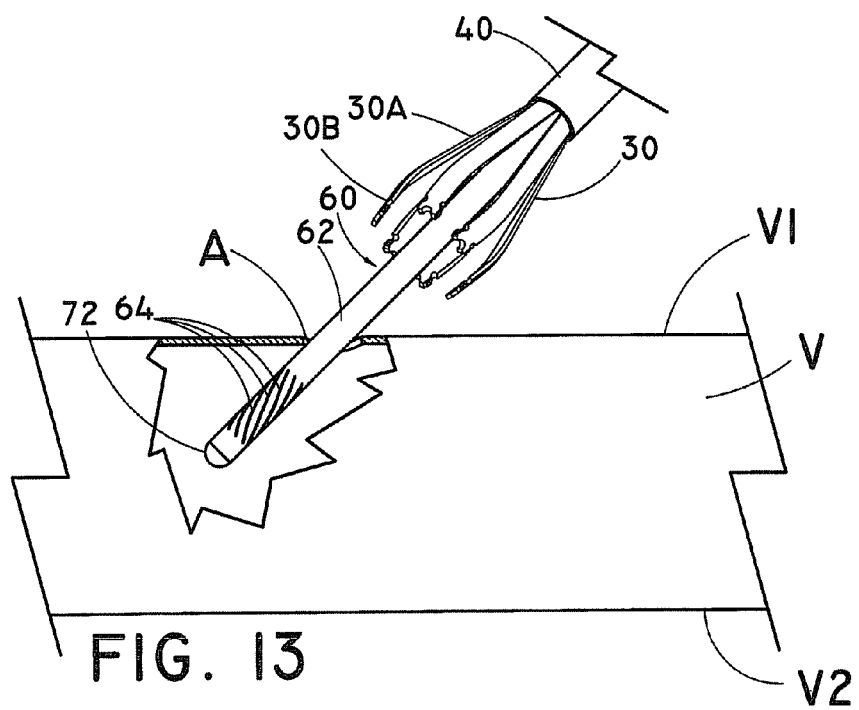
FIG. 13 illustrates the anchor member in combination with the closure device, wherein the distal portion of the anchor member is introduced through the vessel opening while in a non-expanded condition.

FIG. 13 illustrates closure device 20 in combination with optional anchor 60. As grasping fingers 30 approach opening A, the distal portion of anchor 60 is passed through a central passageway of the closure device. Slits 64 extend through opening A, and into the interior space of the vessel. The cannula is urged distally relative to the rod, such that spiral slits 64 bow outwardly to form large diameter anchor portion 68, as described above.

Figure 14:
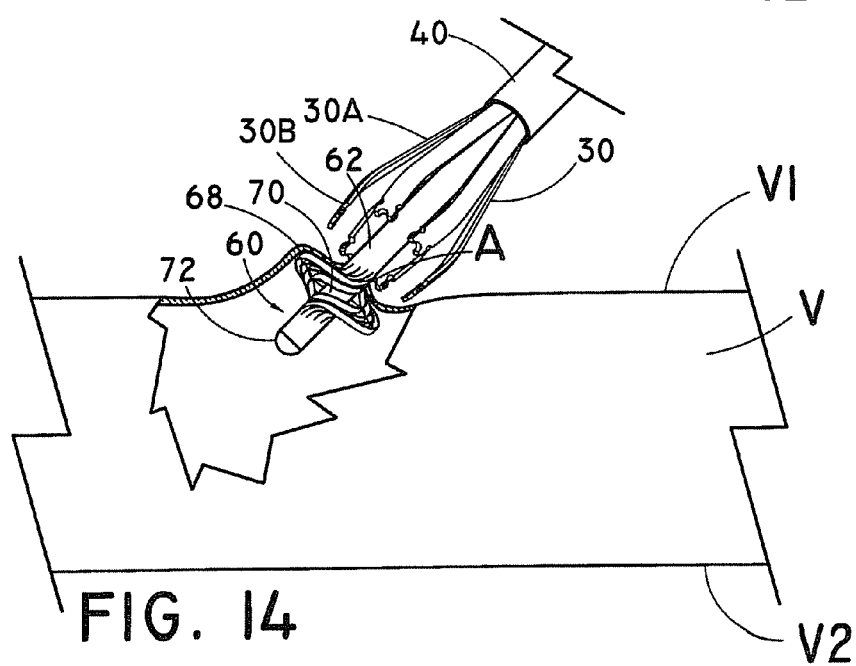
FIG. 14 illustrates the anchor member in combination with the closure device as shown in FIG. 13, wherein the distal portion of the anchor member is shown in an expanded condition.

The presence of large diameter portion 68 within the interior space of the body vessel forms a platform within the interior space of the body vessel. The tissue surrounding the access opening may be aligned on this platform, and manipulated in a manner to provide a suitable surface for receiving the distal tips 34 of fingers 30, as shown in FIG. 14. This arrangement provides the grasping fingers with leverage that assists in closing the wound.

Those skilled in the art will appreciate that other conventional structures having a distal segment capable of radial expansion may be substituted for the particular arrangement of the cannula and rod described above. For example, the anchor member may comprise an expandable balloon, such as a Fogarty balloon. In this case, the balloon is capable of being inserted into the interior of the vessel in a non-expanded condition, and expanded therein to have a larger diameter expanded portion.

Figure 15:
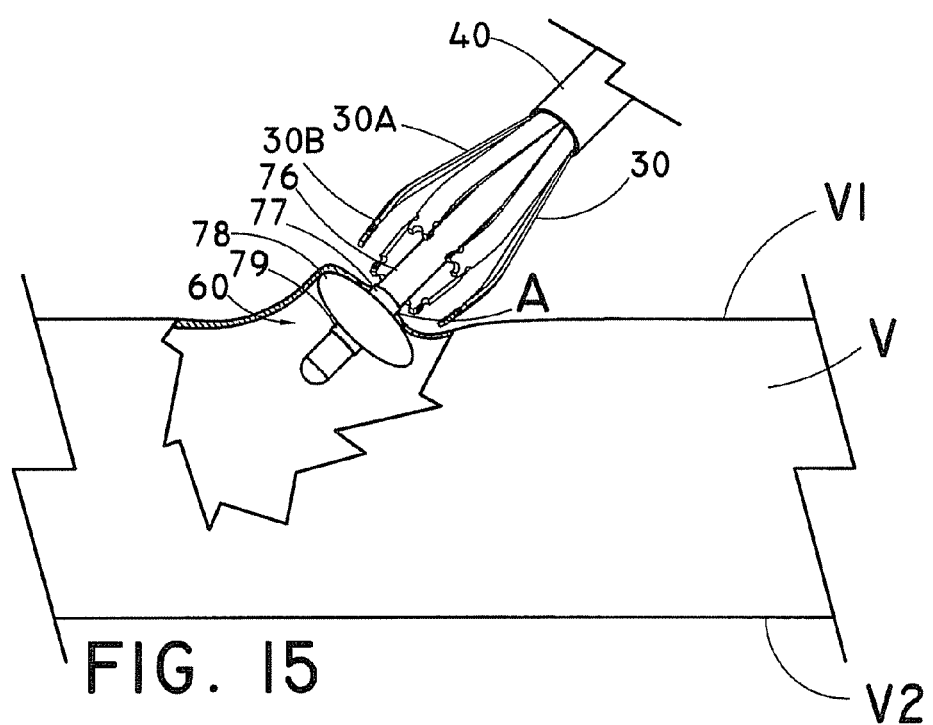
FIG. 15 illustrates use of an expandable balloon as the anchor member.

One non-limiting example of a balloon anchor is illustrated in FIG. 15. The balloon anchor includes a shaft portion 76 and an expandable balloon 78. Balloon 78 includes a proximal end 77 and a distal end 79 in sealing engagement with shaft portion 76 in well-known fashion. Shaft portion 76 communicates with a source of inflation fluid (not shown), and with the interior of balloon 78, in conventional manner for transmitting the fluid into the balloon interior upon inflation of the balloon. Those skilled in the art will appreciate that suitable balloons for use herein may have other expanded geometrical configurations, such as spherical, cylindrical, etc. Expandable balloons are in widespread use in the medical arts, and those skilled in the art can readily select an appropriate balloon for use herein.

Once the tissue surrounding the opening has been grasped and positioned for closure as described hereinabove, the grasping apparatus 20 can maintain contact with the site for a sufficient time to allow clotting and wound healing to occur. It is envisioned that such contact may take approximately 10-30 minutes for sufficient clotting and/or wound healing to occur such that the grasping apparatus can be removed from the access site. Those skilled in the art will appreciate that lesser, or greater, time periods may be appropriate in a particular case.

As an alternative to maintaining continual contact as described above to allow clotting and wound healing to occur, the opening at the access site can be cauterized by applying an electrical current to the site while the closure device is still in place. In this embodiment, an insulator (such as sheath 100) may be applied around a portion of the closure device 20 to protect the surrounding tissue, and an electrosurgical generator 80 may be electrically engaged with the closure device. One non-limiting example of the electrical connection of the optional electrosurgical generator is shown schematically and in phantom in FIG. 8. Those skilled in the art will appreciate that the electrosurgical generator unit could also be included with any of the other embodiments illustrated and/or described herein.

By incorporating the electrosurgical unit 80, electrical current can be passed through the grasping fingers 20 for transmission to the tissue surrounding the access opening. The use of RF current is known in the medical field to be useful for such purposes as resection, coagulation and hemostatic sealing of body openings, such as vessel openings, in both open and laparoscopic surgery. Electrosurgery can be used to cut, coagulate, dessicate, or fulgurate tissue. Among others, its benefits include the ability to make precise cuts with limited blood loss. In this case, the RF current electro-cauterizes the vessel access site to close the opening in well-known manner.

As well known by those skilled in the art, units for generating electrical (e.g. RF) current typically include an electrode and a ground plate. The generated RF current travels from the electrode tip to the access site, and back to the unit via the ground plate. The use of the RF current in this manner promotes faster healing and recovery time. Suitable electrosurgical equipment to carry out such techniques may be obtained commercially.

Those skilled in the art will appreciate that other routine modifications may be made to the vessel closure device as described herein for a particular purpose, which modifications are considered within the scope of the invention. Additional features of the construction or composition of the various elements of the vessel closure device not otherwise discussed herein are not believed to be critical to the present invention, so long as the recited elements possess the capability needed for them to perform as desired. Additional details of construction are believed to be well within the ability of one of ordinary skill in the art.

It is therefore intended that the foregoing detailed description be regarded as illustrative rather than limiting, and that it be understood that it is the following claims, including all equivalents, that are intended to define the spirit and scope of this invention.

The invention claimed is:

1. A device for closure of an opening formed in a body vessel, comprising:
   a grasping member comprising an integral tubular member having a proximal portion and a distal portion, said proximal portion comprising a generally tubular body and said distal portion comprising a plurality of grasping fingers extending from a distal end of said generally tubular body, said fingers being defined by slits through said tubular member, wherein said fingers extend integrally from said tubular body, said fingers having a generally rectangular cross-section defined by a thickness and a width where said width is larger than said thickness, said width being defined by said slits and said thickness being defined by inner and outer surfaces of said tubular member, said fingers radially extending from said tubular body distal end at a first angle, and collapsible therefrom to a second angle, said fingers having a distal tip configured for non-piercingly grasping an outer wall of said body vessel surrounding said opening when said fingers are extended at said first angle, said distal tip including two generally flattened portions at a leading end thereof and a groove disposed between the generally flattened portions, said generally flattened portions each comprising a distally facing end surface defined by at least a portion of said rectangular cross-section; and
   a sheath having a lumen extending therethrough, said lumen sized for receiving at least a portion of said grasping member therein, said sheath slidable over said generally tubular body and at least a portion of said grasping fingers for collapsing said fingers from said first angle to said second angle, thereby causing said collapsed fingers to at least substantially close said opening.

2. The device of claim 1, wherein said fingers include a first segment extending radially from said tubular body distal end at said first angle, and a second segment extending from said first segment at an angle other than said first angle, said distal tip being formed on said second segment.

3. The device of claim 1, further comprising an expandable skirt extending along a length of said fingers.

4. The device of claim 1, wherein said generally tubular body is bendable along a length thereof.

5. The device of claim 4, wherein said generally tubular body includes a spiral slot or a helical coil along said length to provide said bending.

6. The device of claim 1, further comprising an anchor member having a distal end portion, said distal end portion having a non-expanded condition and an expanded condition, said anchor member configured such that said distal end portion is passable through said generally tubular body of said grasping member in said non-expanded condition, and expandable to said expanded condition upon passage therethrough.

7. The device of claim 6, wherein said anchor member comprises a cannula having a plurality of slits formed along said distal end, and a rod receivable within a lumen of said cannula and movable relative to said cannula, said anchor member configured such that said slits bow outwardly upon said relative movement for converting said distal end portion from said non-expanded condition to said expanded condition.

8. The device of claim 6, wherein said anchor member distal end portion comprises a balloon expandable from said non-expanded condition to said expanded condition.

9. The device of claim 1, further comprising an electrosurgical unit capable of passing an electric current through said distal tip of at least some of said fingers, said electric current capable of cauterizing said opening.

10. The device of claim 1, wherein said grasping member comprises a spring metal or nitinol, and said fingers have a length of between about 3 and 15 mm.

11. The device of 1 claim 1, wherein said distal tip further includes a cut-out portion along a lateral side of said fingers, said lateral side extending between said inner and outer surfaces and defining at least one side of said width.

12. The device of claim 11, wherein said grasping member consists of six of said fingers.

13. The device of claim 12, wherein an outer diameter of said grasping member is within 0.75 and 2 mm.

14. The device of claim 1, wherein said distal tip further includes a plurality of teeth along a lateral side of said fingers, said lateral side extending between said inner and outer surfaces and defining at least one side of said width.

15. The device of claim 14, wherein said distal tip further include a cut-out portion along said lateral side of said fingers proximal from said teeth.

16. The device of claim 1, wherein said grasping member consists of six of said fingers.

17. The device of claim 1, wherein an outer diameter of said grasping member is within 0.75 and 2 mm.

18. A method for closure of an opening at an access site in a body vessel, comprising:
    providing a closure device for said opening, said closure device comprising a grasping member comprising a tubular member having an integral proximal portion and distal portion, said proximal portion comprising a generally tubular body and said distal portion comprising a plurality of grasping fingers extending from a distal end of said generally tubular body, said fingers being defined by slits through said tubular member, wherein said fingers extend integrally from said tubular body, said fingers having a generally rectangular cross-section defined by a thickness and a width where said width is larger than said thickness, said width being defined by said slits and said thickness being defined by inner and outer surfaces of said tubular member, said fingers radially extending from said tubular body distal end at a first angle, and collapsible therefrom to a second angle, said fingers having a distal tip configured for non-piercingly grasping tissue of said body vessel surrounding said opening when said fingers are extended at said first angle, said distal tip including two generally flattened portions at a leading end thereof and a groove disposed between the generally flattened portions, said generally flattened portions each comprising a distally facing surface defined by at least a portion of said rectangular cross-section; and an elongated sheath having a lumen extending therethrough, said sheath having a proximal portion and a distal portion, and being slidable over at least a portion of said grasping member;
    arranging said closure device such that said distal tips of said fingers engage said tissue surrounding said opening at said first angle; and
    grasping the proximal portion of the sheath, and sliding said proximal portion in a distal direction, whereby the distal portion of said sheath advances over said grasping member to collapse said fingers from said first angle to said second angle, wherein said fingers move radially to gather said engaged tissue and at least substantially close said opening.

19. The method of claim 18, wherein said generally tubular body is bendable along a length thereof, said method further including the step of bending said tubular body prior to engaging said finger distal tips with said surrounding tissue.

20. The method of claim 18, wherein said closure device further comprises an anchor member having a distal end portion, said distal end portion having a non-expanded condition and an expanded condition, said method further including the step of passing said anchor member distal end portion through said generally tubular body and through said access site opening into an interior space of said vessel in said non-expanded condition, and expanding said distal end portion to said expanded condition upon passage therethrough.

21. The method of claim 20, wherein said anchor member comprises a cannula having a plurality of slits formed along said distal end, and a rod receivable within a lumen of said cannula and movable relative to said cannula, said anchor member configured such that said slits bow outwardly upon said relative movement for converting said distal end portion from said non-expanded condition to said expanded condition, said method further including the step of effecting said relative movement for converting said distal end portion from said non-expanded condition to said expanded condition.

22. The method of claim 20, wherein said anchor member distal end portion comprises a balloon expandable from said non-expanded condition to said expanded condition.

23. The method of claim 18, further comprising the step of passing an electrical current through the grasping fingers to the access site to electro-cauterize the site.

24. The method of claim 18, wherein said distal tip further includes a cut-out portion along a lateral side of the fingers, said lateral side extending between said inner and outer surfaces and defining at least one side of said width.

25. The method of claim 18, wherein said grasping member consists of six of said fingers.

* * * * *

UNITED STATES PATENT AND TRADEMARK OFFICE
CERTIFICATE OF CORRECTION

PATENT NO.        : 9,192,362 B2
APPLICATION NO.   : 13/059157
DATED             : November 24, 2015
INVENTOR(S)       : Ram H. Paul, Jr. et al.

Page 1 of 1

It is certified that error appears in the above-identified patent and that said Letters Patent is hereby corrected as shown below:

In the Claims

In column 10, claim 11, line 49, after "The" replace "device of 1 of claim 1," with --device of claim 1,--.

Signed and Sealed this
Twenty-fourth Day of May, 2016

Michelle K. Lee
*Director of the United States Patent and Trademark Office*